(12) United States Patent  (10) Patent No.: US 7,559,691 B2
Fuhrmann                    (45) Date of Patent:     Jul. 14, 2009

(54) CEILING-MOUNTED X-RAY EXAMINATION DEVICE

(75) Inventor: Michael Fuhrmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 16 days.

(21) Appl. No.: 10/592,291

(22) PCT Filed: Feb. 15, 2005

(86) PCT No.: PCT/EP2005/050661

§ 371 (c)(1),
(2), (4) Date: Jul. 17, 2007

(87) PCT Pub. No.: WO2005/087108

PCT Pub. Date: Sep. 22, 2005

(65) Prior Publication Data

US 2007/0280425 A1   Dec. 6, 2007

(30) Foreign Application Priority Data

Mar. 10, 2004  (DE) .................. 10 2004 011 671

(51) Int. Cl.
   *H05G 1/02*   (2006.01)
   *A61B 6/04*   (2006.01)
(52) U.S. Cl. .................. 378/196; 378/197; 378/209
(58) Field of Classification Search .............. 378/20, 378/196, 197, 198, 209; 5/601
See application file for complete search history.

(56) References Cited

U.S. PATENT DOCUMENTS

| 2,822,477 | A |   | 2/1958  | Kizaur |
|-----------|---|---|---------|--------|
| 3,803,418 | A |   | 4/1974  | Holstrom |
| 4,435,830 | A | * | 3/1984  | Suzuki et al. ............... 378/197 |
| 4,501,011 | A | * | 2/1985  | Hauck et al. ................ 378/196 |
| 5,013,018 | A | * | 5/1991  | Sicek et al. .................... 5/601 |
| 6,045,262 | A | * | 4/2000  | Igeta et al. .................. 378/209 |
| 6,094,760 | A |   | 8/2000  | Nonaka et al. |
| 6,155,713 | A | * | 12/2000 | Watanabe .................... 378/197 |
| 6,256,528 | B1 | * | 7/2001  | Zonneveld et al. .......... 600/425 |
| 6,282,264 | B1 | * | 8/2001  | Smith et al. ................. 378/189 |
| 6,322,251 | B1 | * | 11/2001 | Ballhaus et al. ............. 378/209 |
| 6,456,684 | B1 | * | 9/2002  | Mun et al. ..................... 378/20 |
| 6,733,176 | B2 | * | 5/2004  | Schmitt ....................... 378/196 |
| 6,789,940 | B2 | * | 9/2004  | Meyer et al. ................ 378/196 |
| 6,934,361 | B2 | * | 8/2005  | Ohkoda .................... 378/98.8 |
| 7,478,947 | B2 | * | 1/2009  | Kobayashi .................. 378/181 |
| 2002/0080921 | A1 |  | 6/2002 | Smith et al. |

FOREIGN PATENT DOCUMENTS

| DE | 101 42 441 C1 | 3/2003 |
| EP | 0 430 934 B1  | 6/1991 |
| WO | WO 87/03795 A1 | 7/1987 |
| WO | WO 03/071948 A1 | 9/2003 |

\* cited by examiner

Primary Examiner—Allen C Ho

(57) ABSTRACT

The invention relates to a ceiling-mounted x-ray examination device comprising a patient-receiving table, an X-ray emitter, an X-ray receiver, a first adjusting device mountable on the ceiling for holding or displacing the X-ray emitter and preferably a second adjusting device mountable on the ceiling for holding and is placing the X-ray receiver and a travelling unit for displacing the patient-receiving table at least approximately transversally to the longitudinal direction thereof, wherein a travel path of the patient-receiving table is greater than the width thereof.

16 Claims, 4 Drawing Sheets

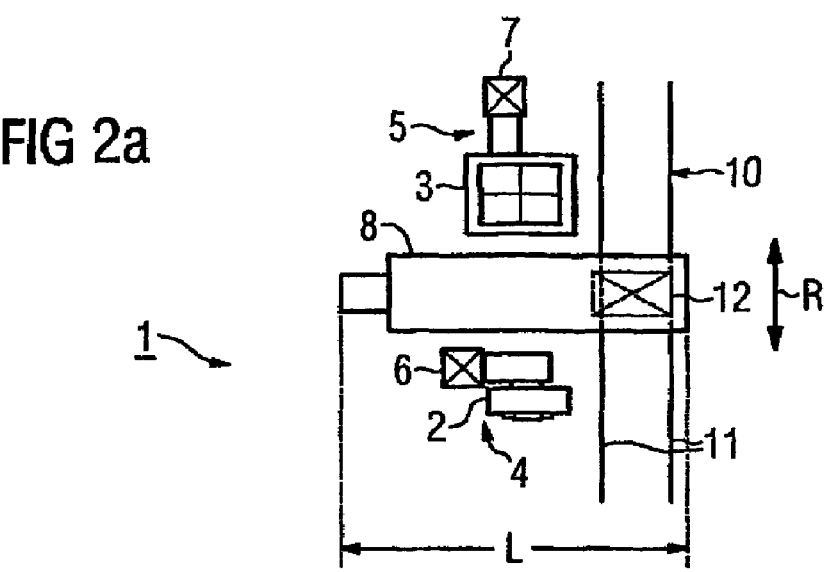
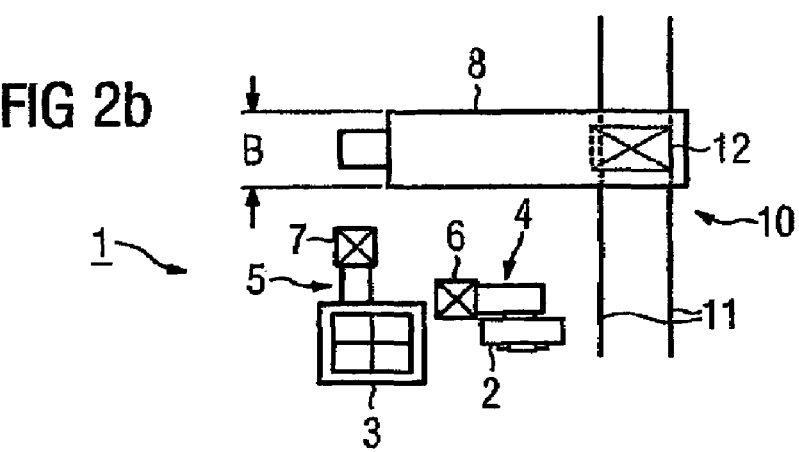
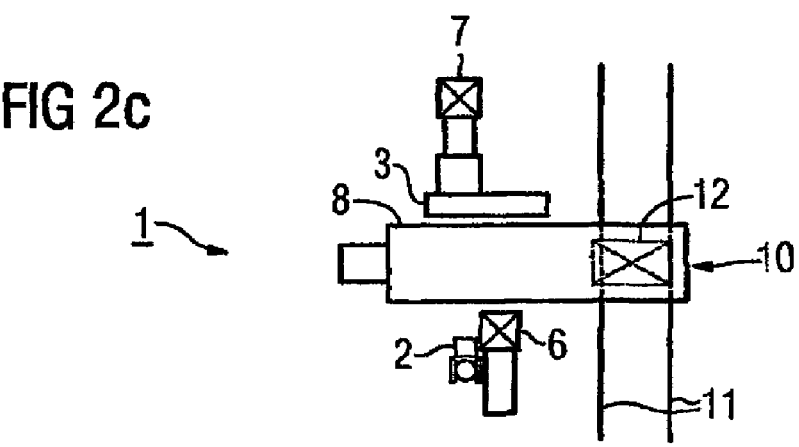

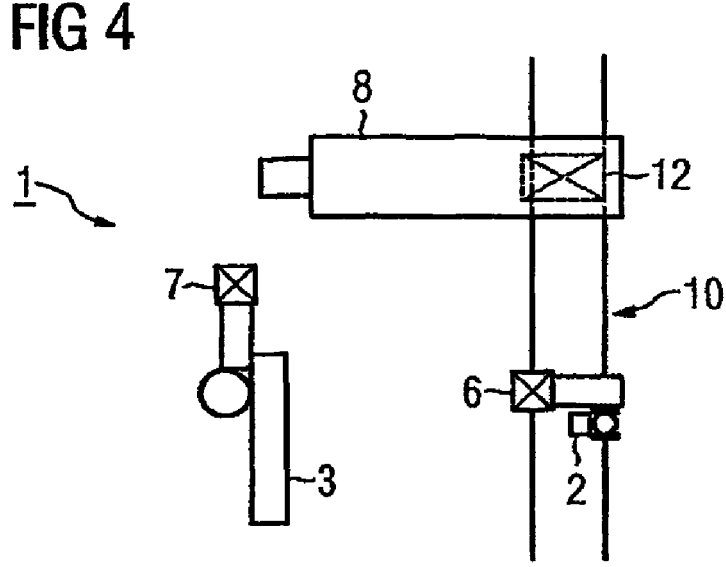
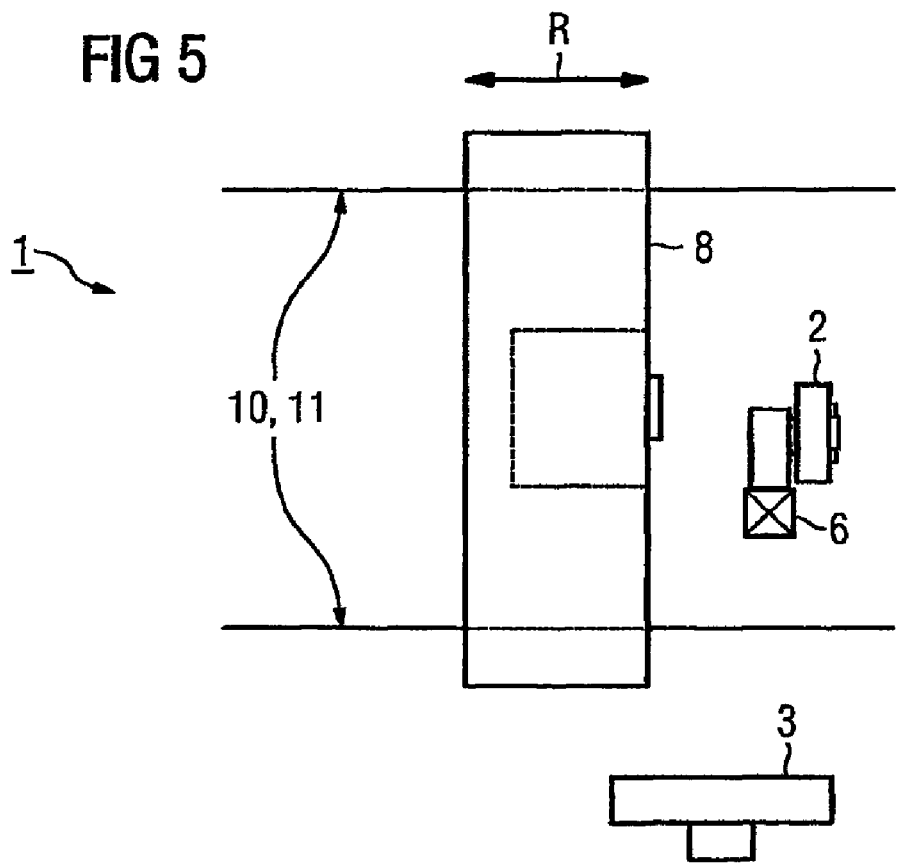

US 7,559,691 B2

CEILING-MOUNTED X-RAY EXAMINATION DEVICE

CROSS REFERENCE TO RELATED APPLICATIONS

This application is the US National Stage of International Application No. PCT/EP2005/050661 filed Feb. 15, 2005 and claims the benefits thereof. The International Application claims the benefits of German application No. 10 2004 011 671.1 filed Mar. 10, 2004, both of the applications are incorporated by reference herein in their entirety.

FIELD OF THE INVENTION

The invention relates to a ceiling-mounted x-ray examination device, with at least an x-ray emitter, in particular also an x-ray receiver, being mounted so as to be movable on the ceiling of an examination room.

BACKGROUND OF THE INVENTION

The x-ray examination device known from US 2002/0080921 A1 comprises a patient table, which for example is arranged on a lifting table. The patient table can also be swiveled around a horizontal and/or vertical axis. Alternatively the patient may also be on a portable stretcher or in a wheelchair during the x-ray examination.

An x-ray examination device is known from EP 0 430 934 B1 which comprises a fixed trestle and a mobile table unit in the form of a portable stretcher. The mobile table unit and the trestle each have locking devices enabling the table unit to click onto the trestle.

An apparatus known from DE 101 42 441 C1 permits flexible use in that individual x-ray components are adjustably suspended. However, the disadvantage of this apparatus is the large amount of space required. In particular, in order to use the unrestricted functionality of the x-ray examination device, it must be possible to access the patient-receiving table from the side without restriction, so that the x-ray emitter and the x-ray receiver can be arranged practically at will around the patient. If a new x-ray examination device of the kind known from DE 101 42 441 C1 is installed in existing examination rooms, originally designed for the use of simpler x-ray equipment, these facilities for adjustment cannot be used to the full in individual cases because of the limited space available.

SUMMARY OF THE INVENTION

The object of the invention is to specify an x-ray examination device having a ceiling-mounted, adjustable x-ray emitter and having an x-ray receiver, permitting flexible use while the same time making particularly good use of space.

The object is achieved according to the invention by an x-ray examination device with the features of the claims. At least an x-ray emitter, preferably also an x-ray receiver, is adjustably suspended here from a ceiling of an examination room. In order to move the patient-receiving table transversely or approximately transversely to the extent of said patient-receiving table, a traveling unit is provided, whose travel path is greater than the width of the patient-receiving table, preferably greater than half the length of the patient-receiving table. In a preferred embodiment the patient-receiving table is motor-driven and can be adjusted by means of the traveling unit. The ability to adjust the patient-receiving table sideways has the particular advantage that it can also be moved near to the wall of an examination room, in order for example to free up an examination space or recording space between x-ray emitter and x-ray receiver, in which a patient who is not located on the patient-receiving table, for example a standing or sitting patient, can be examined. Preferably the patient-receiving table can be displaced by means of the traveling unit, which has components, in particular rails, permanently fixed to the floor of the examination room, via which the entire or almost the entire usable space can be traversed. Depending on the precise design of the adjustable suspension means of the x-ray emitter and of the x-ray receiver, the x-ray examination device can also be used in the conventional way in the various operating modes known from DE 101 42 441 C1. However, in contrast to this the patient-receiving table does not need to be accessible from both longitudinal sides in every operating mode.

The patient-receiving table can be linked in various ways to the traveling unit. In a preferred embodiment the patient-receiving table is eccentrically connected to the traveling unit such that the largest part of the surface of the patient-receiving table projects on one side over the surface area in which the patient-receiving table is connected mechanically to the traveling unit, so that for example it is possible to position the x-ray receiver centrally underneath the patient-receiving table. In an alternative embodiment, which places fewer demands on the mechanical stability of individual components of the traveling unit, the patient-receiving device is guided on rails at least approximately symmetrically on both sides, i.e. on one side in the head area and on the other side in the foot area.

BRIEF DESCRIPTION OF THE DRAWINGS

An exemplary embodiment of the invention is described in greater detail below on the basis of a drawing, in which in a diagrammatic illustration:

FIG. 2 shows an x-ray examination device according to the invention in various operating modes, FIG. 4 shows the x-ray examination device according to FIGS. 2a to 2c in an additional examination position, and FIG. 5 shows an additional exemplary embodiment of an x-ray examination device.

Components corresponding to one another or having the same effect are provided with the same reference characters in all figures.

DETAILED DESCRIPTION OF THE INVENTION

Figure 1:
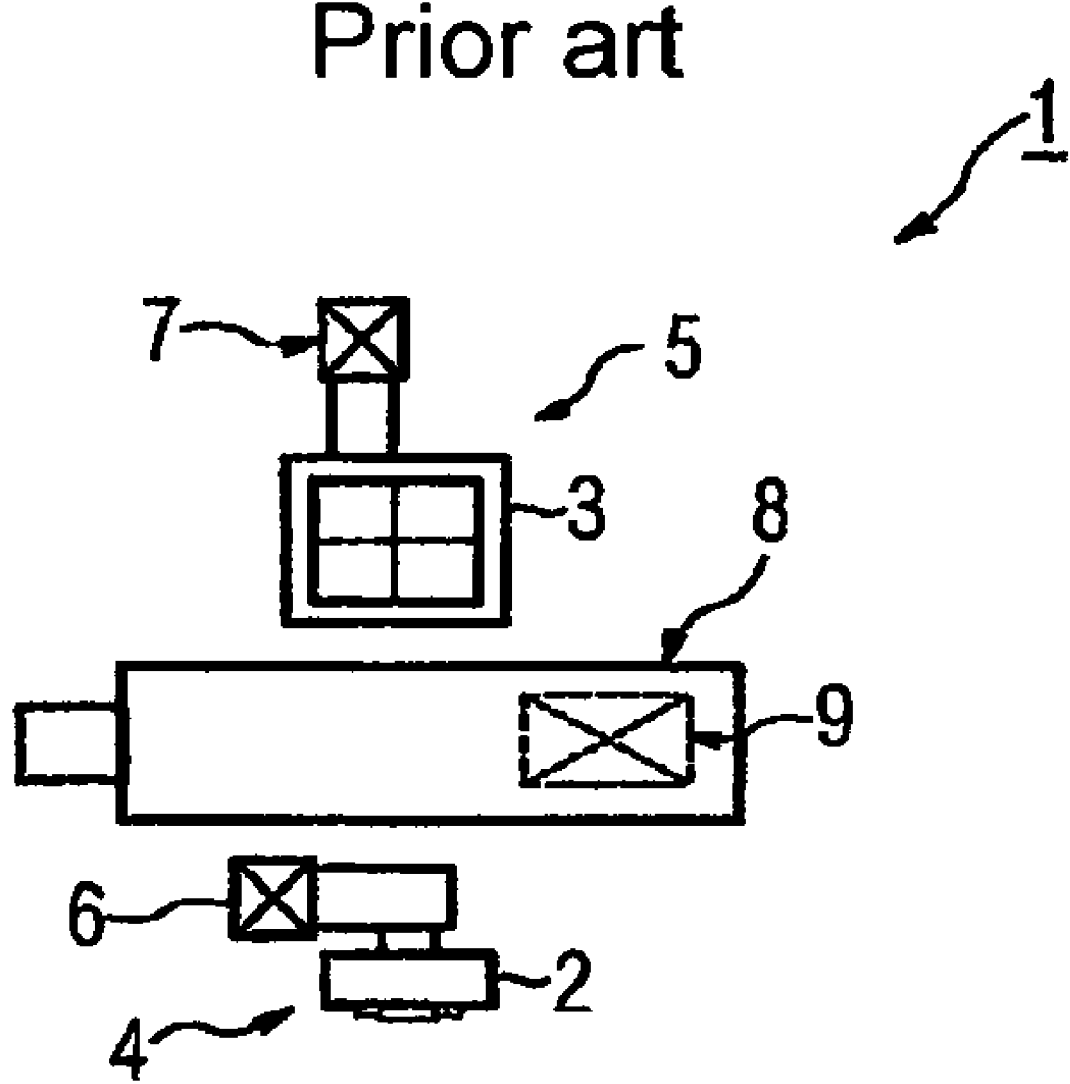
FIG. 1 shows an x-ray examination device according to the prior art.

FIG. 1 shows in simplified form a conventional x-ray examination device 1, as is known in principle for example from DE 101 42 441 C1. The x-ray examination device 1 has an x-ray emitter 2 and an x-ray receiver 3, also called a detector for short. The x-ray components 2, 3 mentioned are each suspended by means of an adjusting device 4, 5 from a ceiling of the examination room in which the x-ray examination device 1 is installed. Each adjusting device 4, 5 comprises a column 6, 7. In the arrangement according to FIG. 1 a patient-receiving table 8 held on a non-movable table foot 9 is located between the x-ray emitter 2 and the detector 3.

FIG. 2a shows an x-ray examination device 1 according to the invention, the arrangement of the patient-receiving table 8, the x-ray emitter 2 and the detector 3 in principle corresponding to the arrangement according to FIG. 1. In contrast to this however, the patient-receiving table 8, whose length is designated by L, is not attached to a table foot permanently mounted in the examination room, but is mounted on a traveling unit 10 which enables the patient-receiving table 8 to be moved in the transverse direction R, i.e. transversely to the longitudinal direction of the patient-receiving table 8. The traveling unit 10 comprises two rails 11 on the floor of the examination room and a table stand 12 which can be moved on the rails 11 and supports the patient-receiving table 8 instead of the table foot 9 according to FIG. 1. The traveling unit is motor-driven, preferably remotely, and is designed mechanically such that it is not possible for the patient-receiving table 8 to tilt. The traveling unit 10 including the table stand 12 only extends over barely one third of the length L of the patient-receiving table 8, so that the latter is very easily accessible from all sides, in particular also from below. Thus the x-ray emitter 2 and the x-ray receiver 3 can be positioned virtually at will around the patient-receiving table 8.

In the arrangement according to FIG. 2b the x-ray emitter 2 and the detector 3 are located on the same side of the patient-receiving table 8, which in this case is not used when taking the x-ray. Instead the patient can for example stand or sit next to the patient-receiving table 8 while the x-ray is taken. The patient-receiving table 8 can then travel almost up to the wall of the examination room. The travel path of the patient-receiving table 8 is significantly greater than the width B thereof and at least as great as half its length L. Even when space overall is cramped, a patient who is not on the patient-receiving table 8 but for example is in a bed, on a trolley or in a wheelchair can be examined using the x-ray examination device 1. X-rays of the thorax are equally as possible in this case as examinations of the extremities.

The positioning of the x-ray examination device 1 according to FIG. 2c corresponds in essence to the positioning according to FIG. 2a. In contrast however, the x-ray emitter 2 and the detector 3 have an angular position, as is required for examining a patient situated on the patient-receiving table 8. An x-ray transversely across the patient-receiving table 8 is thus possible, it being possible to set a favorable, space-saving positioning of the individual components 2, 3, 8 of the x-ray examination device 1 in the case of different emitter-detector distances on the basis of the movable patient-receiving table 8. In particular, by displacing the patient-receiving table 8, the distance between the detector 3 and the patient-receiving table 8 can be reduced, without requiring more space overall. In all operating modes the traveling unit 10 ensures that the x-ray emitter 2, also called tubes, can be optimally positioned, as can the detector 3, preferably designed as a flat detector, relative to the patient-receiving table 8.

Figure 3C:
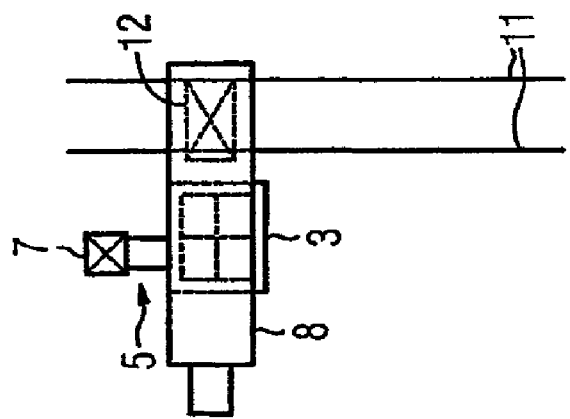
FIG. 3 shows sections of the x-ray examination device according to FIGS. 2a to 2c in different positions intended for the preparation and performance of an examination.
Figure 3B:
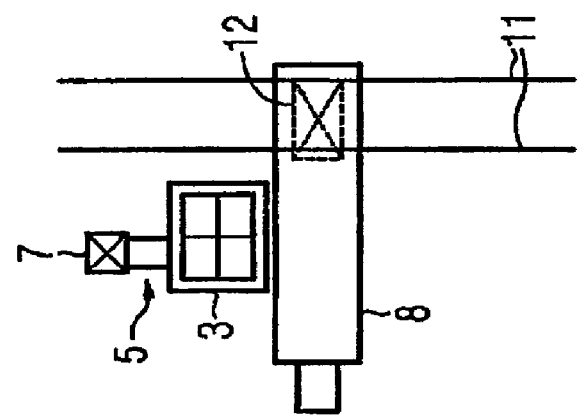
Figure 3A:
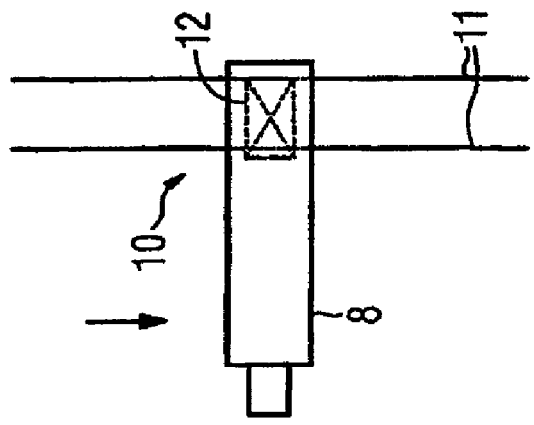

FIGS. 3a to 3c show the x-ray examination device 1 without an x-ray emitter 2 during the performance and preparation of an x-ray examination. As indicated in FIG. 3a by an arrow, the patient-receiving table 8 travels by means of the traveling unit 10 initially approximately into the middle of the examination room. Then, as shown in FIG. 3b, the detector 3 is brought into the position required for the x-ray examination. The position of the patient-receiving table 8 remains unchanged during this procedure. In the next step, as shown in FIG. 3c, the patient-receiving table 8 is traversed over the detector 3, which in this case is stationary. In the case of a stationary patient-receiving table 8 in the position shown in FIG. 3c, it would not be possible to displace the detector 3 into the position underneath the patient-receiving table 8 because of the restricted space. In contrast, the traveling unit 10 permits extremely flexible, ergonomically favorable use of the x-ray examination device 1 even when the adjusting devices 4, 5 are not far away from the walls (not shown) of the examination room. The movements of the adjusting devices 4, 5 and of the traveling unit 10 are synchronized by means of a controller (not shown) of the x-ray examination device 1. Various organ programs harmonized with the respective medical requirements are available here for various examinations.

FIG. 4 shows, analogously to FIG. 2b, a positioning of the x-ray examination device 1 in which the patient-receiving table 8 is outside the recording area while the x-ray is being taken. The arrangement according to FIG. 4 is preferably selected when taking x-rays of patients standing in front of the table. Depending on the layout of the examination room, the space on the side of the patient-receiving table 8 facing away from the x-ray components 2, 3 can also be used in this case.

The x-ray examination device 1 shown in FIG. 5 permits, as do the devices according to FIGS. 2a to 4, both the examination of a patient located on a patient-receiving table 8 and also of a standing patient. Unlike the previously mentioned exemplary embodiments, however, in the arrangement according to FIG. 5 no provision is made for arranging the detector 3 underneath the patient-receiving table 8. Also, unlike the x-ray emitter 2, the detector 3 in the exemplary embodiment according to FIG. 5 is not necessarily suspended from the ceiling of the examination room. This permits a mechanically simplified design of the traveling unit 10, which in this case has two rails 11 running approximately symmetrically in the region of both ends of the patient-receiving table 8. The x-ray receiver 3 is located in the illustrated diagrammatic plan view outside the surface of the patient-receiving table 8 and above a plane defined by the patient-receiving table 8. By moving the patient-receiving table 8 by means of the traveling unit 10 the patient-receiving table 8 can be positioned in front of the detector 3, in which case lateral cartridge recordings from the front or the back are possible. It is not necessary to move the patient for this, since the patient-receiving table 8 can be accessed from both sides.

The invention claimed is:

1. A ceiling-mounted medical x-ray examination device, comprising:
    an x-ray receiver;
    an x-ray emitter;
    a ceiling mounted adjusting device for holding and moving the x-ray emitter;
    a patient-receiving table that supports a patient;
    a rail; and
    a traveling unit permanently mounted on the rail, the traveling unit configured to hold and move the patient-receiving table in a direction transverse to the longitudinal direction of the patient-receiving table a distance that is greater than a width of the patient-receiving table so that the patient-receiving table can be moved out of a recording space between the x-ray emitter and the x-ray receiver when moved in a direction transverse to the longitudinal direction of the patient-receiving table, to free up the recording space,
    wherein the recording space comprises the center of the patient-receiving table, and
    wherein the x-ray examination device comprises another adjusting device that is ceiling-mounted for holding and moving the x-ray receiver.

2. The x-ray examination device as claimed in claim 1, wherein the traveling unit is motor-driven.

3. The x-ray examination device as claimed in claim 2, wherein the traveling unit is remotely motor-driven.

4. The x-ray examination device as claimed in claim 1, wherein the patient-receiving table is connected eccentrically to the traveling unit.

5. The x-ray examination device as claimed in claim 4, wherein the patient-receiving table is connected to the traveling unit only on one side over less than half of a length of the patient-receiving table.

6. The x-ray examination device as claimed in claim 1, wherein the patient-receiving table is connected symmetrically to the traveling unit.

7. The x-ray examination device as claimed in claim 1, wherein the rail is on a floor of an examination room.

8. The x-ray examination device as claimed in claim 1, wherein the traveling unit is permanently mounted on two rails.

9. A method for a medical x-ray examination device having a traveling unit for moving a patient-receiving table, comprising:
- arranging an x-ray emitter on a ceiling mounted adjusting device,
- arranging an x-ray receiver;
- supporting a patient on the patient-receiving table; and
- mounting the traveling unit on a rail for supporting and moving the patient-receiving table in a direction transverse to the longitudinal direction of the patient-receiving table a distance that is greater than a width of the patient-receiving table so that the patient-receiving table is moved out of a recording space between the x-ray emitter and the x-ray receiver when moved in a direction transverse to the longitudinal direction of the patient-receiving table, to free up the recording space,
- wherein the recording space comprises the center of the patient-receiving table, and
- wherein the rail is on a floor of an examination room.

10. The method as claimed in claim 9, wherein the traveling unit is permanently mounted on the rail.

11. The method as claimed in claim 9, wherein the x-ray examination device comprises two ceiling-mounted adjusting devices for holding and moving the x-ray emitter and the x-ray receiver respectively.

12. The method as claimed in claim 9, wherein the traveling unit is motor-driven.

13. The method as claimed in claim 12, wherein the traveling unit is remotely motor-driven.

14. The method as claimed in claim 9, wherein the patient-receiving table is connected eccentrically to the traveling unit.

15. The method as claimed in claim 14, wherein the patient-receiving table is connected to the traveling unit only on one side over less than half of a length of the patient-receiving table.

16. The method as claimed in claim 9, wherein the patient-receiving table is connected symmetrically to the traveling unit.

* * * * *